(12) United States Patent
Sun (10) Patent No.: US 10,370,419 B2
(45) Date of Patent: Aug. 6, 2019

(54) TUBERCULOSIS VACCINE COMPOSITIONS AND RELATED METHODS

(71) Applicant: BOARD OF REGENTS, THE UNIVERSITY OF TEXAS SYSTEM, Austin, TX (US)

(72) Inventor: Jianjun Sun, El Paso, TX (US)

(73) Assignee: THE BOARD OF REGENTS OF THE UNIVERSITY OF TEXTAS SYSTEM, Austin, TX (US)

( * ) Notice: Subject to any disclaimer, the term of this patent is extended or adjusted under 35 U.S.C. 154(b) by 0 days.

(21) Appl. No.: 15/533,434

(22) PCT Filed: Dec. 9, 2015

(86) PCT No.: PCT/US2015/064822
§ 371 (c)(1),
(2) Date: Jun. 6, 2017

(87) PCT Pub. No.: WO2016/094574
PCT Pub. Date: Jun. 16, 2016

(65) Prior Publication Data
US 2018/0037616 A1    Feb. 8, 2018

Related U.S. Application Data (60) Provisional application No. 62/089,295, filed on Dec. 9, 2014.

(51) Int. Cl.
| | | |
|---|---|---|
| *A61K 39/02* | (2006.01) |
| *C07K 14/35* | (2006.01) |
| *A61K 39/04* | (2006.01) |
| *G01N 33/569* | (2006.01) |
| *A61K 39/00* | (2006.01) |

(52) U.S. Cl.
CPC .............. *C07K 14/35* (2013.01); *A61K 39/04* (2013.01); *G01N 33/5695* (2013.01); *A61K 2039/522* (2013.01); *G01N 2333/35* (2013.01)

(58) Field of Classification Search
None
See application file for complete search history.

(56) References Cited

U.S. PATENT DOCUMENTS

| 8,398,991 B2 | 3/2013 | Brosch et al. ............. 424/200.1 |
| 2005/0272104 A1 | 12/2005 | Chan et al. ................. 435/7.32 |

FOREIGN PATENT DOCUMENTS

| WO | WO/95/001441 | 1/1995 |
| WO | WO/02/004018 | 1/2002 |
| WO | WO/03/066820 | 8/2003 |

OTHER PUBLICATIONS

Greenspan et al (Nature Biotechnology 7: 936-937, 1999).*
Chothia et al (The Embo Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
International Search Report and Written Opinion in International Application No. PCT/US2015/064822 dated Mar. 16, 2016.
International Preliminary Report on Patentability in International Application No. PCT/US2015/064822 dated Jun. 13, 2017.

* cited by examiner

*Primary Examiner* — Jennifer E Graser
(74) *Attorney, Agent, or Firm* — Norton Rose Fulbright US LLP (57) ABSTRACT

Compositions and methods directed to ESAT-6 variants which serve as vaccines for the prevention and prophylactic treatment of TB.

16 Claims, 7 Drawing Sheets

Specification includes a Sequence Listing.

MTEQQWNFAG IEAAASAIQG NVTSIHSLLD
EGKQSLTKLA AAWGGSGSEA YQGVQQKWDA
TATELNNALQ NLARTISEAG QAMASTEGNV TGMFA

TUBERCULOSIS VACCINE COMPOSITIONS AND RELATED METHODS

CROSS-REFERENCE TO RELATED APPLICATION

This application is a national phase application under 35 U.S.C. § 371 of International Application No. PCT/US2015/064822, filed Dec. 9, 2015, which claims the benefit of the filing date of U.S. Provisional Patent Application No. 62/089,295 filed on Dec. 9, 2014, by the inventor of this application. Both of which are incorporated herein in their entirety.

REFERENCE TO SEQUENCE LISTING

A sequence listing required by 37 CFR 1.821-1.825 is being submitted electronically with this application. The sequence listing is incorporated herein by reference.

TECHNICAL FIELD OF THE INVENTION

The present disclosure relates generally to tuberculosis vaccine compositions and related methods. More particularly, the disclosure relates to methods for making mutant variants of the ESAT-6 polypeptides and the resulting compositions thereof. These compositions serve as vaccine candidates for the tuberculosis prevention and treatment.

BACKGROUND

According to the World Health Organization (WHO), *Mycobacterium tuberculosis* (Mtb or *M. tuberculosis*), a contagious and airborne bacterial pathogen, infects one third of the world population. As noted by the Centers for Disease Control and Prevention (CDC), tuberculosis (TB) is caused by exposure to Mtb which usually attack the lungs. However, TB bacteria may attack any part of the body such as the kidney, spine, and brain. If not treated properly, TB disease can be fatal. In 2012 alone, there were 8.6 million new human cases and 1.3 million deaths caused by TB. However, not every human infected with TB bacteria becomes ill. As a result, two TB-related conditions exist: latent TB infection and TB disease.

Latent TB infection involves asymptomatic exposure to TB bacteria. In most people who breathe in TB bacteria and become infected, the body is able to fight the bacteria to stop them from growing. People with latent TB infection do not feel sick and do not have any symptoms. People with latent TB infection are not infectious and cannot spread TB bacteria to others.

However, if TB bacteria become active in the body and multiply, the person will go from having latent TB infection to being sick with TB disease. TB bacteria become active if the immune system is compromised and thus unable to counter Mtb growth. When TB bacteria are active (multiplying), this is called TB disease. People with TB disease are sick and infectious. This may lead to the development of additional latent TB exposure and active TB disease in others.

Many people who have latent TB infection never develop TB disease. Some people develop TB disease soon after becoming infected (within weeks) before their immune system can fight the TB bacteria. Other people may get sick years later when their immune system becomes weak for another reason. For people whose immune systems are weak, especially those with HIV infection, the risk of developing TB disease is much higher than for people with normal immune systems.

Thus, TB-HIV co-infection and the emergence of multi-drug resistant TB are posing an unprecedented threat to public health. Failure to control the TB epidemic is largely due to lack of effective vaccines against TB. The current and the only approved TB vaccine is *Mycobacterium bovis bacillus* Calmette-Guerin (BCG), which is an attenuated strain of *M. bovis*. BCG has been used for nearly 100 years and is the most widely used TB vaccine worldwide. While BCG provides protection against TB in newborns, it does not prevent the establishment of latent TB or reactivation of pulmonary TB in adults. There remains a need for additional vaccine compositions and related methods of use and treatment for TB.

SUMMARY

In view of the aforementioned problems and trends, general embodiments of the present disclosure provide compositions and methods for producing a vaccine against tuberculosis. These compositions and methods are useful for the prevention and therapeutic treatment of tuberculosis.

Certain embodiments are directed to engineered polypeptides and compositions comprising the same, as well as methods of using the polypeptides and compositions described herein.

In certain aspects a recombinant protein comprises all or part of the amino acid sequence of the 6-kDal early secreted antigenic target (ESAT-6) polypeptide.

Wild type ESAT-6 can have an amino acid sequence of MTEQQWNFAGIEAAASAIQGNVTSIHSLIDEGKQSLT-KLAAAWGGSGSEAYQGVQQ KWDATATELNNALQN-LARTISEAGQAMASTEGNVTGMFA (SEQ ID NO:1).

In a certain aspect the ESAT-6 peptide includes one or more mutations in residues important for cell membrane lysis. In certain other aspects the recombinant ESAT-6 protein serves as a vaccine composition.

Certain aspects of the disclosure are directed to a vaccine for tuberculosis (TB) which includes a recombinant ESAT-6 protein as disclosed herein.

Other aspects of the present disclosure include compositions that contain or do not contain a bacterium. A composition may or may not include an attenuated or viable or intact *Mycobacterium* bacterium (e.g., *Mycobacterium tuberculosis*).

In certain additional aspects, a composition includes an isolated or recombinantly expressed *Mycobacterium* ESAT-6 variant or a nucleotide encoding the same. The composition may be or include a recombinantly engineered *Mycobacterium* bacterium that has been altered in a way that comprises specifically altering the bacterium with respect to ESAT-6 protein. For example, the bacteria may be recombinantly modified to express more of the ESAT-6 variants described herein than it would express if unmodified.

In some aspects, the protein is provided directly by administering the protein, while in other aspects, the protein is effectively provided by administering a nucleic acid encoding the protein. Certain other aspects of the disclosure contemplate compositions that include various combinations of nucleic acid, antigens, peptides, and/or epitopes.

In certain aspects relating to diagnostic use, a subject will have (e.g., being diagnosed with a *mycobacterium* infection, e.g., a *M. tuberculosis* infection), will be suspected of having, or will be at risk of developing a *Mycobacterium* infection.

Compositions of the present disclosure include immunogenic compositions wherein the antigen(s) or epitope(s) are contained in an amount effective to achieve the intended purpose.

Other embodiments of the invention are discussed throughout this application. Any embodiment discussed with respect to one aspect of the invention applies to other aspects of the invention as well and vice versa. Each embodiment described herein is understood to be an embodiment of the invention that is applicable to other aspects of the invention. It is contemplated that any embodiment discussed herein can be implemented with respect to any method or composition of the invention, and vice versa. Furthermore, compositions and kits of the invention can be used to achieve methods of the invention.

Other aspects of the embodiments described herein will become apparent from the following description and the accompanying drawings, illustrating the principles of the embodiments by way of example only.

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

FIG. 3a depicts the aligned ESAT-6 amino acid sequences from M. tuberculosis (SEQ ID NO: 1), M. bovis (SEQ ID NO: 2), M. marinum (SEQ ID NO: 3), and M. smegmatis (SEQ ID NO: 4) while FIG. 3b depicts the structure of the MtbESAT-6/CFP-10 heterodimer, FIG. 4a illustrates the time-lapse measurements of ANTS fluorescence intensity while FIG. 4b is a graph of the membrane-interacting activities of MtbESAT-6, MsESAT-6 and their mutants, FIG. 7a is a graph of relative membrane-interacting activities (ANTS fluorescence) of the indicated MtbESAT-6 mutants while FIG. 7b is the graph of ANS fluorescence of the indicated MtbESAT-6 mutants at either pH 7 or pH 5 solutions. FIGS. 7c and d are the graphs of Trp emission spectra of MtbESAT-6 and MtbESAT-6(IH/TA-17 mutant at either pH 7 or pH 5 solutions.

NOTATION AND NOMENCLATURE

Certain terms are used throughout the following description and claims to refer to particular system components and configurations. As one skilled in the art will appreciate, the same component may be referred to by different names. This document does not intend to distinguish between components that differ in name but not function.

The term "providing" is used according to its ordinary meaning to indicate "to supply or furnish for use."

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Thus, they should be interpreted to mean "including, but not limited to . . . ."

Protein Composition(s):

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed in generating an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function. It is specifically contemplated that a modified/variant protein or polypeptide may be altered with respect to one activity or function yet retain a wild-type activity or function in other respects, such as immunogenicity.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a polypeptide or peptide of the invention. In certain aspects, the adjuvant is chemically conjugated to a protein, polypeptide, or peptide.

As used herein, an "amino molecule" refers to any amino acid, amino acid derivative, or amino acid mimic known in the art. In certain embodiments, the residues of the proteinaceous molecule are an amino molecule which is sequential, without any non-amino molecule interrupting the sequence of amino molecule residues. In other embodiments, the sequence of the proteinaceous molecule may comprise one or more non-amino molecule moieties. In particular embodiments, the sequence of residues of the proteinaceous molecule may include one or more amino molecules interrupted by one or more non-amino molecule moieties/molecules.

Accordingly, the term "proteinaceous composition" encompasses amino molecule sequences comprising at least one of the 20 common amino acids in naturally synthesized proteins, or at least one modified or unusual amino acid.

The term "functionally equivalent codon" is used herein to refer to codons that encode the same amino acid, such as the six codons for arginine or serine, and also refers to codons that encode biologically equivalent amino acids: Alanine (A) GCA, GCC, GCG, GCU; Cysteine (C) UGC, UGU; Aspartic acid (D) GAC, GAU; Glutamic acid (E) GAA, GAG; Phenylalanine (F) UUC, UUU; Glycine (G) GGA, GGC, GGG, GGU; Histidine (H) CAC, CAU; Isoleucine (I) AUA, AUC, AUU; Lysine (K) AAA, AAG; Leucine (L) UUA, UUG, CUA, CUC, CUG, CUU; Methionine (M) AUG; Asparagine (N) AAC, AAU; Proline (P) CCA, CCC, CCG, CCU; Glutamine (Q) CAA, CAG; Arginine (R) AGA, AGG, CGA, CGC, CGG, CGU; Serine (S) AGC, AGU, UCA, UCC, UCG, UCU; Threonine (T) ACA, ACC, ACG, ACU; Valine (V) GUA, GUC, GUG, GUU; Tryptophan (W) UGG; and Tyrosine (Y) UAC, UAU.

Nucleic Acid(s):

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. It also is contemplated that a particular polypeptide may be encoded by nucleic acids containing variations having slightly different nucleic acid sequences but, nonetheless, encode the same or substantially similar protein.

As used herein the phrase "immune response" or its equivalent "immunological response" refers to the development of a humoral (antibody mediated), cellular (mediated by antigen-specific T cells or their secretion products) or both humoral and cellular response directed against a protein in a recipient patient. Such a response can be an active response induced by administration of immunogen or a passive response induced by administration of antibody, antibody containing material, or primed T-cells.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

The foregoing description of the figures is provided for the convenience of the reader. It should be understood, however, that the embodiments are not limited to the precise arrangements and configurations shown in the figures. Also, the figures are not necessarily drawn to scale, and certain features may be shown exaggerated in scale or in generalized or schematic form, in the interest of clarity and conciseness. The same or similar parts may be marked with the same or similar reference numerals.

While various embodiments are described herein, it should be appreciated that the present invention encompasses many inventive concepts that may be embodied in a wide variety of contexts. The following detailed description of exemplary embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. The scope of the invention is defined by the appended claims and equivalents thereof.

Illustrative embodiments of the invention are described below. In the interest of clarity, not all features of an actual implementation are described in this specification. In the development of any such actual embodiment, numerous implementation-specific decisions may need to be made to achieve the design-specific goals, which may vary from one implementation to another. It will be appreciated that such a development effort, while possibly complex and time-consuming, would nevertheless be a routine undertaking for persons of ordinary skill in the art having the benefit of this disclosure.

*Mycobacterium tuberculosis*, the causative pathogen of human pulmonary tuberculosis (TB) diseases, causes ~9 million new cases of active TB and kills over 1 million people each year worldwide. It is estimated that nearly ⅓ of the world population is latently infected by *M. tuberculosis* and 5-10% of the latently infected individuals develop active TB. Thus, the transition of latent infection to active TB diseases is a critical step for TB control. At the early stage of infection, *M. tuberculosis* is internalized into the phagosomes of host macrophages, where it establishes latency probably through inhibiting phagosome maturation. At the later stage of infection, however, transition to active TB requires the latent *M. tuberculosis* rupture the phagosomal membranes and translocate into the cytosol, where *M. tuberculosis* replicates for cell-to-cell spreading.

The ability of the pathogen to arrest phagosome maturation and to translocate from the phagosome to the cytosol has been attributed, at least in part, to the newly identified Type VII secretion system (named ESX-1) and its effector proteins. Comparative and functional genomic analysis have found a chromosomal region, named "region of different 1" (RD1), which is present in the genome of virulent *M. tuberculosis*, but is absent in the genome of the attenuated vaccine stain *Mycobacterium bovis* Bacille Calmette-Guérin (BCG). Deletion of RD1 from *M. tuberculosis* attenuated virulence, while transfer of RD1 into BCG partially restored virulence. The RD1 was located to the esx-1 locus that comprises 11 genes encoding the ESX-1 secretion system and two secreted effector proteins: 6-kDa early-secreted antigenic target (ESAT-6, also called EsxA or Rv3875) and 10-kDa culture filtrate protein (CFP-10, also called EsxB or Rv3874).

The genes of esat-6 and cfp-10 are under the control of a single operon. While both ESAT-6 and CFP-10 lack N-terminal Sec or TAT signal sequences, they are exported as a heterodimer by the ESX-1 secretion system in a co-dependent manner. The secreted ESAT-6/CFP-10 clearly plays an important role in mycobacterial virulence, since loss or gain of mycobacterial virulence is closely linked to the ability of mycobacteria to produce and secrete ESAT-6/CFP-10. Mycobacterial strains carrying the mutations that abolish production or secretion of ESAT-6/CFP-10 exhibited attenuated virulence, while introduction of ESX-1 or RD1 to restore ESAT-6/CFP-10 secretion resulted in increased virulence in BCG and *Mycobacterium microti*.

More specifically, ESAT-6/CFP-10 has been implicated in the above mentioned phagosome-to-cytosol translocation of mycobacteria. Gaining cytosolic access has multiple consequences in mycobacterial infection, including mycobacterial replication and cell-to-cell spreading as well as host cell apoptosis, autophagy induction or impairment, type-I interferon release, and T-cell response. Moreover, recent studies have suggested that even prior to full-fledged phagosomal rupture, ESAT-6 may permeabilize the phagosomal membrane to expose mycobacterial DNA to the host cytosolic DNA-sensing pathway.

Figure 3:
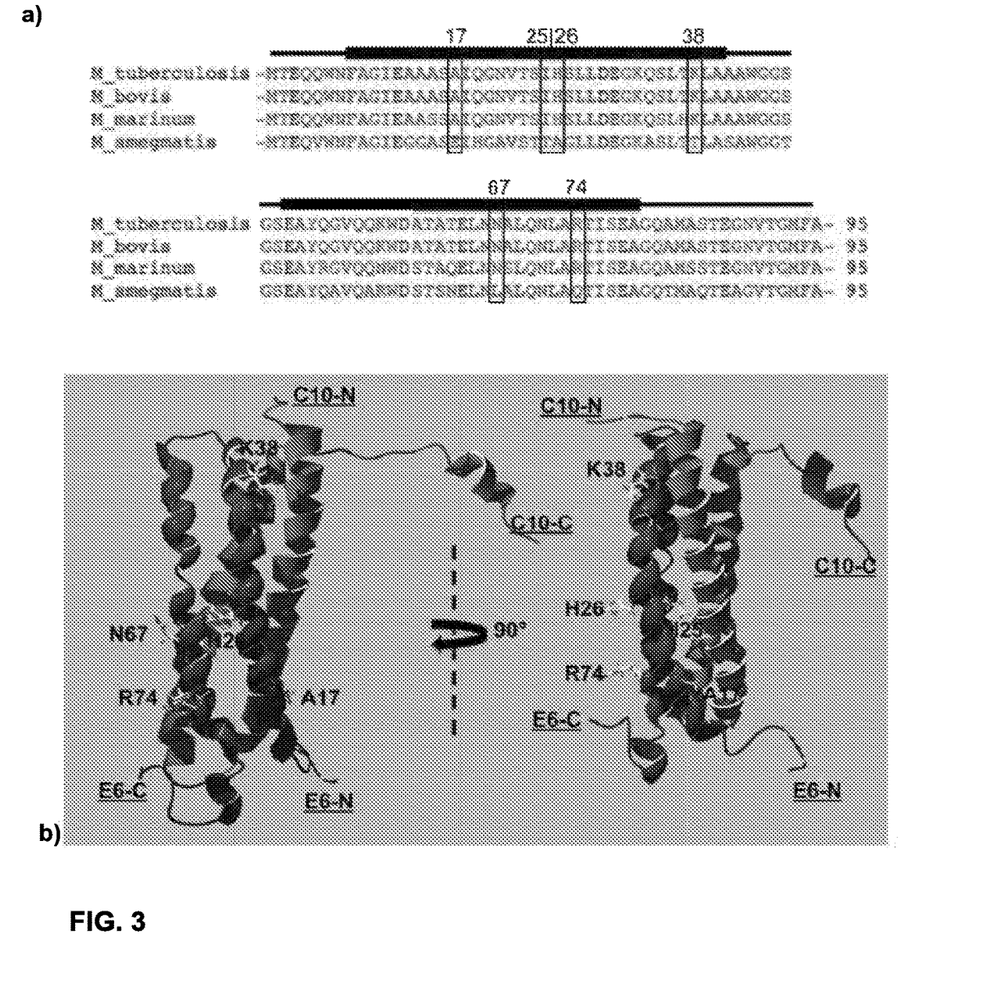

Biochemical and structural studies have showed that ESAT-6 and CFP-10 form a 1:1 heterodimeric complex, and ESAT-6 exhibits membrane-lysis activity. Thus, it is believed that the membrane-interacting activity of ESAT-6 plays a role in *M. tuberculosis* cytosolic translocation within host macrophages, however, the molecular mechanism of ESAT-6 membrane interaction is not clear. In our earlier reports, we have demonstrated that upon acidification the central Helix-turn-Helix motif of ESAT-6 inserts into the membrane and forms a membrane-spanning pore. We have also found that the membrane-interacting activity is unique to *M. tuberculosis* ESAT-6 (MtbESAT-6), but it is not found in its ortholog from the non-pathogenic *Mycobacterium smegmatis* (MsESAT-6), even though MsESAT-6 shares ~76% homology with MtbESAT-6 (FIG. 3A). This has promoted us to investigate the differential membrane-interacting activities between MtbESAT-6 and MsESAT-6, which has led to identification of the key residues essential for membrane interaction.

The use of vaccines to prevent tuberculosis in humans has proved to be a tremendous challenge for almost a century now. BCG, derived from *M. bovis*, is currently the only tuberculosis vaccine in use and is the most widely used vaccine in the world. The development and generalized administration of the BCG vaccine since the beginning, of the 1920s represented a significant advance, with the prospect of being able to eradicate tuberculosis from the world. However, these initial promises were not achieved and, from the results of a large number of efficacy trials, it is clear that the BCG vaccine in its current form is of limited use in controlling the disease, particularly in respiratory forms in adults in third world areas where the disease is endemic. With more knowledge of the virulence of *M. tuberculosis* (Mtb) and immune response models that lead to the generation of protective immunity, it is possible to develop vaccines better than BCG. The observation that higher protection levels are achieved when the host is vaccinated with BCG suggests that viability and persistence are fundamental properties required for the success of a tuberculosis vaccine.

Figure 1:
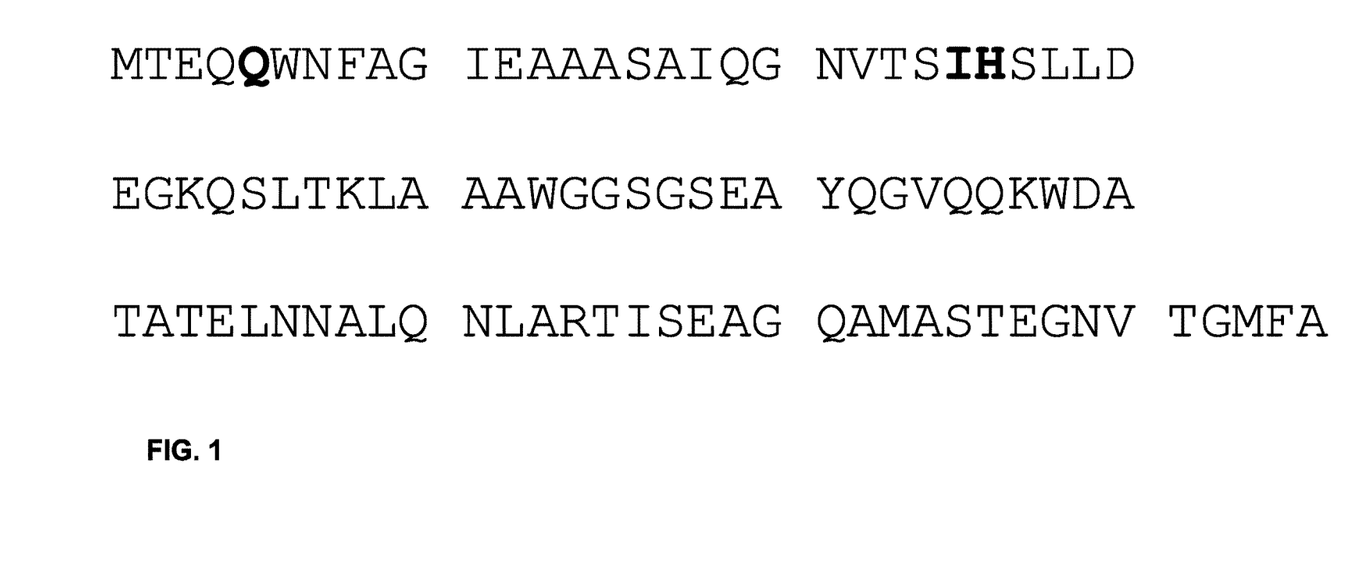
FIG. 1 depicts the amino acid sequence of the wild type (WT) ESAT-6 protein (SEQ ID NO.1)
Figure 2:
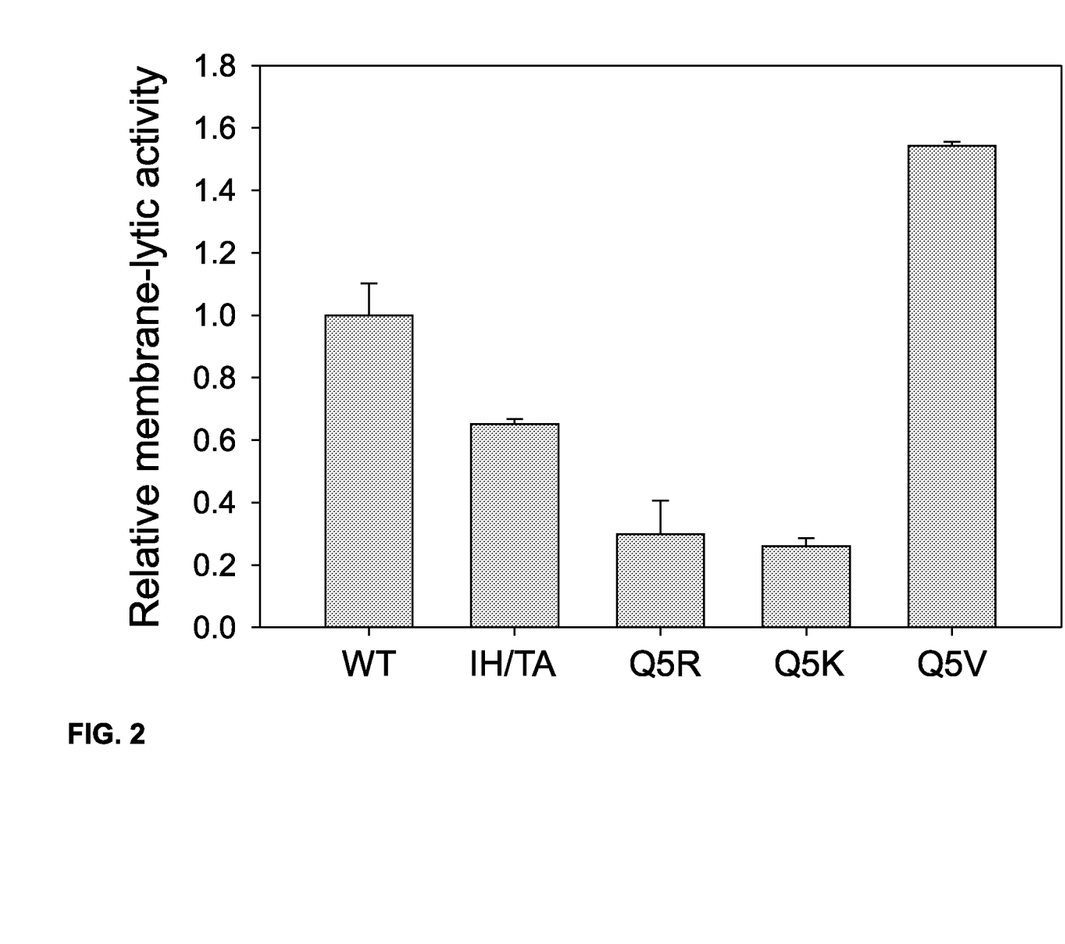
FIG. 2 illustrates the relative membrane-lytic activity of ESAT-6 mutants.

Recent studies have suggested that ESAT-6 is not only a potent antigen, but also a virulence factor essential for *M. tuberculosis* infection. In particular, the recombinant ESAT-6 protein is able to break cell membranes resulting in the lysis of human cells. Thus, there is a great concern of cytotoxicity or side-effects when ESAT-6 wild type (WT) protein is used as a vaccine. Interestingly, 3 out of 14 vaccine candidates in clinical trials are recombinant protein vaccines composed of ESAT-6. As disclosed herein, at least two locations in the ESAT-6 protein are required for the membrane-lytic activity (FIG. 2).

As previously noted, a "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function. It is specifically contemplated that a modified/variant protein or polypeptide may be altered with respect to one activity or function yet retain a wild-type activity or function in other respects, such as immunogenicity.

In certain embodiments the size of a protein or polypeptide (wild-type or modified) may comprise, but is not limited to 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As previously noted, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be known to those of ordinary skill in the art.

Amino acid sequence variants of ESAT-6 can be substitutional, insertional, or deletion variants. A variation in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to wild-type. A variant can comprise an amino acid sequence that is at least 50%, 60%, 70%, 80%, 90%, 91%, 92%, or 93% identical, including all values and ranges there between, to SEQ ID NO:1. A variant can include 1, 2, 3, 4, 5, 6, 7, 8, 9, 10, 11, 12, 13, 14, 15, 16, 17, 18, 19, 20, or more substitute amino acids.

Deletion variants typically lack one or more residues of the native or wild type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptide or polypeptide described or referenced herein.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins of the invention may be recombinant, or synthesized in vitro. Alternatively, a non-recombinant or recombinant protein may be isolated from bacteria. It is also contemplated that a bacterium containing such a variant may be implemented in compositions and methods of the invention. Consequently, a protein need not be isolated.

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create a variant polypeptide or peptide. For example, certain amino acids may be substituted for other amino acids in a protein structure with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence, and in its underlying DNA coding sequence, and nevertheless produce a protein with a desirable property. It is thus contemplated that various changes may be made in the DNA sequences of genes.

It is contemplated that in compositions of the invention, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 5, 10, 15, 20, 25, 30, 35, 40, 45, 50, 55, 60, 65, 70, 75, 80, 85, 90, 95, or 100% may be an ESAT-6 variant, and may be used in combination with other peptides or polypeptides, such as other bacterial peptides and/or antigens.

The present invention contemplates the administration of variant ESAT-6 polypeptides or peptides as a preventative therapy or therapeutic effect against the development of a disease or condition associated with infection by a *mycobacterium* pathogen.

Polypeptides and Polypeptide Production

The present invention describes polypeptides, peptides, and proteins and immunogenic fragments thereof for use in various embodiments of the present invention. For example, specific polypeptides are assayed for or used to elicit an immune response. In specific embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference.

Alternatively, recombinant DNA technology may be employed wherein a nucleotide sequence which encodes a peptide of the invention is inserted into an expression vector, transformed or transfected into an appropriate host cell and cultivated under conditions suitable for expression.

Immunogenic proteins or fragments thereof also include polypeptides that when administered at an effective dose, (either alone or as a hapten bound to a carrier), elicit a protective or therapeutic immune response against *Mycobacterium* infection, in certain aspects it is protective against *Mycobacterium tuberculosis* infection.

Also included in immunogenic compositions of the invention are fusion proteins composed of ESAT-6 protein or immunogenic fragments thereof. Such fusion proteins may be made recombinantly and may comprise one portion of at least 1, 2, 3, 4, 5, or 6 proteins or segments. Alternatively, a fusion protein may comprise multiple portions of at least 1, 2, 3, 4, or 5 proteins. These may combine different proteins and/or multiples of the same protein or protein fragment, or immunogenic fragments in the same protein (forming a multimer or a concatamer). Alternatively, the invention also includes individual fusion proteins of ESAT-6 or immunogenic fragments thereof, as a fusion protein with heterologous sequences, for example: β-galactosidase, glutathione-S-transferase, green fluorescent proteins (GFP), epitope tags such as FLAG, myc tag, poly-histidine, or viral surface proteins such as influenza virus haemagglutinin, or bacterial proteins such as tetanus toxoid, diphtheria toxoid, or CRM197.

Nucleic Acids

As previously noted, "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide. It also is contemplated that a particular polypeptide may be encoded by nucleic acids containing variations having slightly different nucleic acid sequences but, nonetheless, encode the same or substantially similar protein.

In certain embodiments, the present invention concerns recombinant polynucleotides encoding the proteins, polypeptides, peptides of the invention. The nucleic acid sequences for ESAT-6 and ESAT-6 variants are included and can be used to prepare peptides or polypeptides.

In particular embodiments, the invention concerns isolated nucleic acid segments and recombinant vectors incorporating nucleic acid sequences that encode a variant ESAT-6. The term "recombinant" may be used in conjunction with a polynucleotide or polypeptide and generally refers to a polypeptide or polynucleotide produced and/or manipulated in vitro or that is a replication product of such a molecule. For example, recombinant polypeptides with the following mutations [ESAT-6 mutants designated by the amino acid residue(s) of interest] may embody various aspects of the disclosure: Q5, I25H26, A17, K38, N67 and R74.

In other embodiments, the invention concerns isolated nucleic acid segments and recombinant vectors incorporating nucleic acid sequences that encode a variant ESAT-6 polypeptide or peptide to generate an immune response in a subject. In various embodiments the nucleic acids of the invention may be used in genetic vaccines.

Immune Response and Assays

Certain aspects concern evoking or inducing an immune response in a subject against a variant ESAT-6 protein. In one embodiment, the immune response can protect against or treat a subject having, suspected of having, or at risk of developing an infection or related disease, particularly those related to tuberculosis.

The present invention includes the implementation of serological assays to evaluate whether and to what extent an immune response is induced or evoked by compositions of the invention. There are many types of immunoassays that can be implemented. Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In some embodiments of the invention, proteinaceous compositions confer protective immunity to a subject. Protective immunity refers to a body's ability to mount a specific immune response that protects the subject from developing a particular disease or condition that involves the agent against which there is an immune response. An immunogenically effective amount is capable of conferring protective immunity to the subject.

A method of the present invention includes treatment for a disease or condition caused by a *mycobacterium* pathogen. An immunogenic polypeptide of the invention can be given to induce an immune response in a person infected with *mycobacterium* or suspected of having been exposed to *mycobacterium*. Methods may be employed with respect to individuals who have tested positive for exposure to *mycobacterium* or who are deemed to be at risk for infection based on possible exposure.

In some embodiments, the treatment is administered in the presence of adjuvants or carriers or other mycobacterial antigens. Furthermore, in some examples, treatment comprises administration of other agents commonly used against bacterial infection, such as one or more antibiotics.

The use of peptides for vaccination can require, but not necessarily, conjugation of the peptide to an immunogenic carrier protein, such as hepatitis B surface antigen, keyhole limpet hemocyanin, or bovine serum albumin. Methods for performing this conjugation are well known in the art.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Newly Identified ESAT-6 Mutants for Development of Novel Tuberculosis Vaccines Characterization of the membrane-lytic activity of ESAT-6 has shown two locations in the ESAT-6 protein that are required for the membrane-lytic activity.

The recombinant proteins of ESAT-6 wild type (WT) and the indicated mutants were expressed and purified. The membrane-lytic activity was measured by the liposome-based ANTX/DPX fluorescence dequenching assay. The relative membrane-lytic activity of ESAT-6 WT and the mutants were calculated from at least three independent experiments.

One location is at the fifth residue Glutamine (Gln or Q) and the other location is at the 25-26 residues, Isoleucine (Ile or I) and Histidine (His or H). Replacement of IH to TA partially inhibited the membrane-lytic activity of ESAT-6 (~40% of inhibition). Replacement of Q5 with Lysine (Lys or K) or Arginine (Arg or R) nearly completely deleted the ESAT-6 membrane-lytic activity (~80% of inhibition), while replacing Q5 with Valine (Val or V) significantly increased the membrane-lytic activity (FIG. 2).

Thus, the data suggest that IH play a role in the membrane-lytic activity probably by serving as the pH-senor that allows ESAT-6 to make pH-dependent conformational changes. More importantly, the data show that Q5 or the residues at the fifth position have the capacity to up- or down-regulate the membrane-lytic activity of ESAT-6. This is an extremely exciting finding that will be very useful for vaccine development, because one can produce a series of ESAT-6 mutants with different levels of membrane-lytic activity by replacing Q5 with different residues. Moreover, since the mutations are only involved one or two residues of ESAT-6, it will not likely change the process of antigen-presentation of ESAT-6. Therefore, the ESAT-6 mutants, such as IH/TA, Q5/R, or Q5/K, can be used for development of vaccines with similar or better efficacy, but with fewer side effects. This will be a significant improvement for the ESAT-6-based vaccines in clinical trials.

Example 2: Mutagenesis Studies of MtbESAT-6 and MsESAT-6

The 6-kDa early secreted antigenic target protein (MtbESAT-6, EsxA or Rv3875) functions as an important virulence factor of *Mycobacterium tuberculosis*. MtbESAT-6 plays an essential role in phagosome rupture and mycobacterial cytosolic translocation within the host macrophages. Our early study has shown that MtbESAT-6 exhibits a unique membrane-interacting activity that is not found in its ortholog from non-pathogenic *Mycobacterium smegmatis* (MsESAT-6). Since MtbESAT-6 and MsESAT-6 share ~76% sequence homology, it promotes us to investigate the mechanism underlying the differential membrane-interacting activities between the two proteins. Using site-directed mutagenesis and various biochemical approaches, we have found that exchange of the residues I25-H26/T25-A26 between MtbESAT-6 and MsESAT-6 reciprocally affected their membrane-interacting activities. MtbESAT-6(IH/TA) had ~40% of reduction in the activity, while MsESAT-6(TA/IH) had an increased activity to a level seminar to MtbESAT-6. Exchange of the residues A17/E17, K38/T38, N67/L67 or R74/Q74 one at a time on MtbESAT-6(IH/TA) further reduced the activity, with MtbESAT-6(IH/TA-17) having the lowest activity (~10% of MtbESAT-6). This study has identified I25-H26 as the key pH-sensing residues essential for MsESAT-6 to fully restore its membrane-interacting activity. In additional to I25-H26, however, multiple residues are required for MtbESAT-6 to interact with membranes.

Materials and Methods

Genes, Constructs and Site-Directed Mutagenesis—

The full-length MtbESAT-6 and Ms-ESAT-6 with a C-terminal His$_6$ tag were cloned into pET22b at the Nde I/Xho I sites as previously described. The mutations of MtbESAT-6 and MsESAT-6 were generated by site-directed mutagenesis using the QuickChange mutagenesis kit. All of the mutations were confirmed by DNA sequencing.

Expression and Purification of the Recombinant Proteins of MtbESAT-6, MsESAT-6 and the Mutants—

All of the proteins (MtbESAT-6, MsESAT-6 and the mutants) were expressed and purified from bacterial inclusion body as previously described by the inventor in Ma, Y., Keil, V., and Sun, J. (2015) Characterization of *Mycobacterium tuberculosis* EsxA membrane insertion: roles of N- and C-terminal flexible arms and central helix-turn-helix motif. J. Biol. Chem. 290, 7314-7322 and De Leon, J., Jiang, G., Ma, Y., Rubin, E., Fortune, S., and Sun, J. (2012) *Mycobacterium tuberculosis* ESAT-6 Exhibits a Unique Membrane-Interacting Activity That Is Not Found in Its Ortholog from Non-pathogenic *Mycobacterium smegmatis*. J. Biol. Chem. 287, 44184-44191, incorporated herein by reference, in their entirety.

Briefly, the proteins were expressed in BL21 (DE3) at 37° C. The inclusion body was isolated and then solubilized in 8 M urea. The proteins were refolded on a Ni-column and eluted with an imidazole gradient. The eluted proteins were further cleaned by a sizing exclusion chromatography to ~90% pure.

Liposome Preparation—

Liposomes were prepared using conventional techniques. Specifically, 1, 2-Dioleoyl-sn-glycero-3-phosphocholine (DOPC) (20 mg/ml in chloroform) was dried under nitrogen gas to form a lipid film, followed by vacuum for overnight to remove residual solvent. For the liposomes containing the dye/quencher pair, 8-aminonapthalene-1,3,6 trisulfonic acid (ANTS)/p-xylene-bis-pyridinium bromide (DPX), the resulting dry lipid film was rehydrated by six freeze-thaw cycles in 50 mM ANTS, 50 mM DPX, 5 mM HEPES (pH 7.3), followed by extrusion through a 200-nm filter (Nucleopore) in a mini-extruder (Avanti Polar Lipids). Subsequently, the liposome solution was applied to a G-25 desalting column equilibrated with 10 mM HEPES (pH 7.4) and 150 mM NaCl for buffer exchange. The resulting liposome solution has ANTS/DPX inside the liposomes, while the solution outside is free of fluorescence dye.

The Time-Lapse Intensity Measurement of ANTS/DPX Dequenching—

Figure 4:
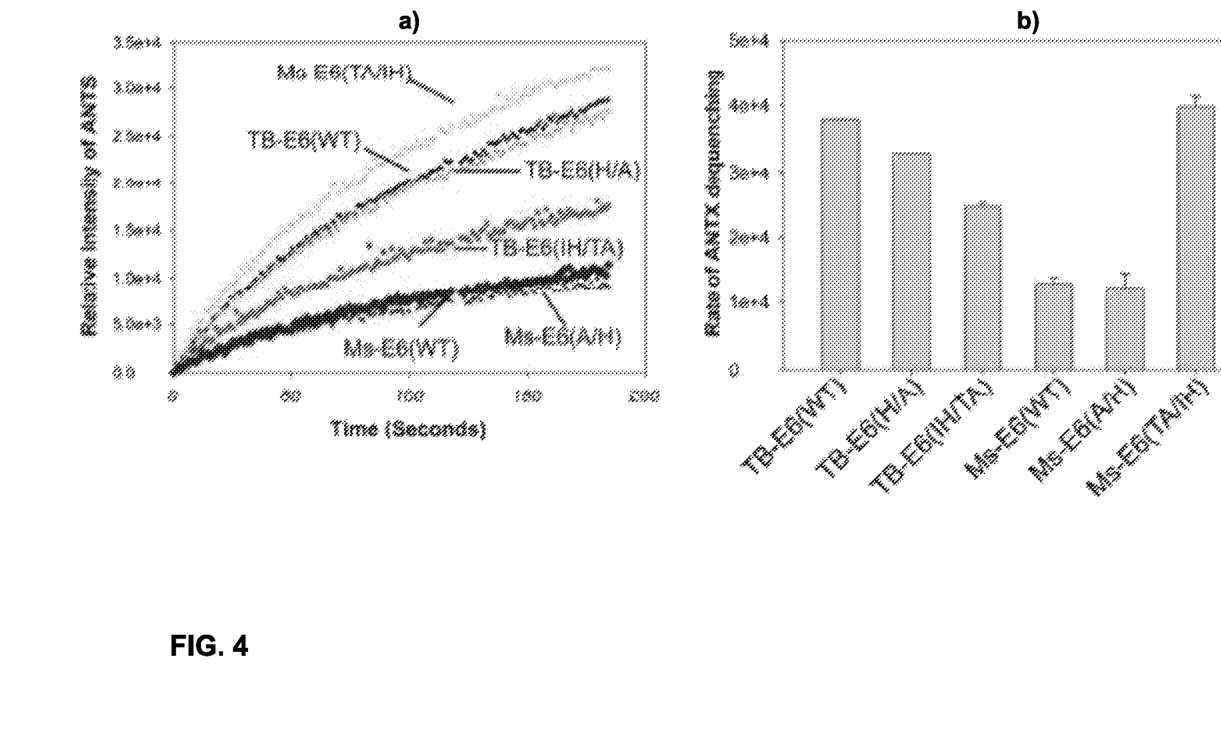

The ANTS fluorescence dequenching was measured as previously described in an ISS-K2 multiphase frequency and modulation fluorometer with excitation at 380 nm and emission at 520 nm (FIG. 4). Specifically, 100 µl of the liposomes containing ANTS/DPX after desalting was diluted into 1.3 ml of 50 mM NaAc, 150 mM NaCl (pH 5.0)

with continuous stirring. After the base line was stabilized, 100 μl of purified proteins (total 100 μg) was injected into the cuvette, and the fluorescence signal was monitored in real-time. Crossed polarizers on excitation and emission beams, and a 395-nm long-path filter were used to reduce the background scatter.

Intrinsic Tryptophan (Trp) Fluorescence—

10 μM of the purified proteins were incubated either in a neutral pH buffer (20 mM TrisHCl, 100 mM NaCl, pH 7.0) or an acidic buffer (20 mM NaAc, 100 mM NaCl, pH 5.0) for 30 min. The intrinsic tryptophan fluorescence was measured in the ISS-K2 fluorometer with excitation at 295 nm and emission at 310-450 nm. A 305 nm long-path filter was applied in the emission channel to reduce the background. The emission spectra of the proteins were calibrated with the emission spectra of the same pH buffers without proteins in VINCI software.

ANS Fluorescence—

5 μM of the purified proteins were incubated with 100 μM of 8-anilino-1-naphthalenesulfonate (ANS) in either pH 7.0 or pH 5.0 buffers for 30 min at dark. The ANS emission spectra of the samples were measured in the ISS-K2 fluorometer with excitation at 380 nm and emission at 400-600 nm. A 395 nm long-path filter was placed in the emission path to reduce the backgrounds. The emission spectra of the samples were calibrated with the same buffers (pH 7 or pH 5) without proteins in VINCI software.

Exchange of the Residues IH/TA Between MtbESAT-6 and MsESAT-6 Reciprocally Affected their Membrane-Interacting Activities.

To identify the residues responsible for differential membrane-interaction, we aligned the ESAT-6 sequences from M. tuberculosis, M. Bovis, M. marinum, and M. smegmatis (FIG. 3A). MtbESAT-6 shares 100%, 92% and 72% identity with MbvESAT-6, MmESAT-6 and MsESAT-6, respectively. Apparently, the ESAT-6 orthologs from pathogenic mycobacteria all have membrane-interacting activity. Thus, it was predicted that the residues that are common in pathogenic ESAT-6 orthologs, but different in MsESAT-6 may be the key residues responsible for the differential membrane-interacting activity. Furthermore, even though MsESAT-6 is not active in membrane interaction, it shares most of the hydrophobic residues with the pathogenic ESAT-6 orthologs. Thus, it is likely that the inability of MsESAT-6 to interact with the membrane at acidic pH is not due to lack of overall hydrophobicity, but due to lack of pH-sensing residue(s) that triggers conformational changes upon acidification.

Based on the foregoing, the 25-26 residues, where I25-H26 is conserved in the pathogenic ESAT-6 orthologs, but not in MsESAT-6 (T25-A26) were determined to be of interest for structure/function studies. In the structures of MtbESAT-6/CFP-10 heterodimer, the residues I25-H26 are located on the center of Helix 1 of MtbESAT-6, with the side chain of H26 exposed to the solution (FIG. 3B). Considering that both Helix 1 and 2 of MtbESAT-6 insert into the membrane and form a membrane-spanning pore, it is highly likely that I25-H26 play an important role in membrane interaction upon acidification.

To confirm the role of I25-H26 in membrane interactions upon acidification, site-directed mutagenesis was used to generate the single-exchange mutants (H/A) or double-exchange mutants (IH/TA) of MtbESAT-6 and MsESAT-6. These mutants were then tested for their membrane-interacting activity using the ANTS fluorescence dequenching assay as previously described. As predicted, exchange of either H/T or IH/TA reciprocally affected the membrane-interacting activities of MtbESAT-6 and MsESAT-6 (FIG. 4). Compared to MtbESAT-6(WT), MtbESAT-6(H/A) and MtbESAT-6(IH/TA) had ~16% and ~40% of reduction in membrane disruption, respectively. Compare to MsESAT-6 (WT), MsESAT-6(A/H) had little change in the activity. Surprisingly, however, MsESAT-6(TA/IH) had a significantly increased activity that is similar to that of MtbESAT-6(WT). This result suggests that replacing TA with IH fully restored MsESAT-6 membrane-interacting activity, while mutating IH to TA only partially reduced MtbESAT-6 activity.

Upon Acidification MsESAT-6(TA/IH) Exhibited an Increased Solvent-Exposed Hydrophobicity that was Equivalent to MtbESAT-6(WT).

Figure 5:
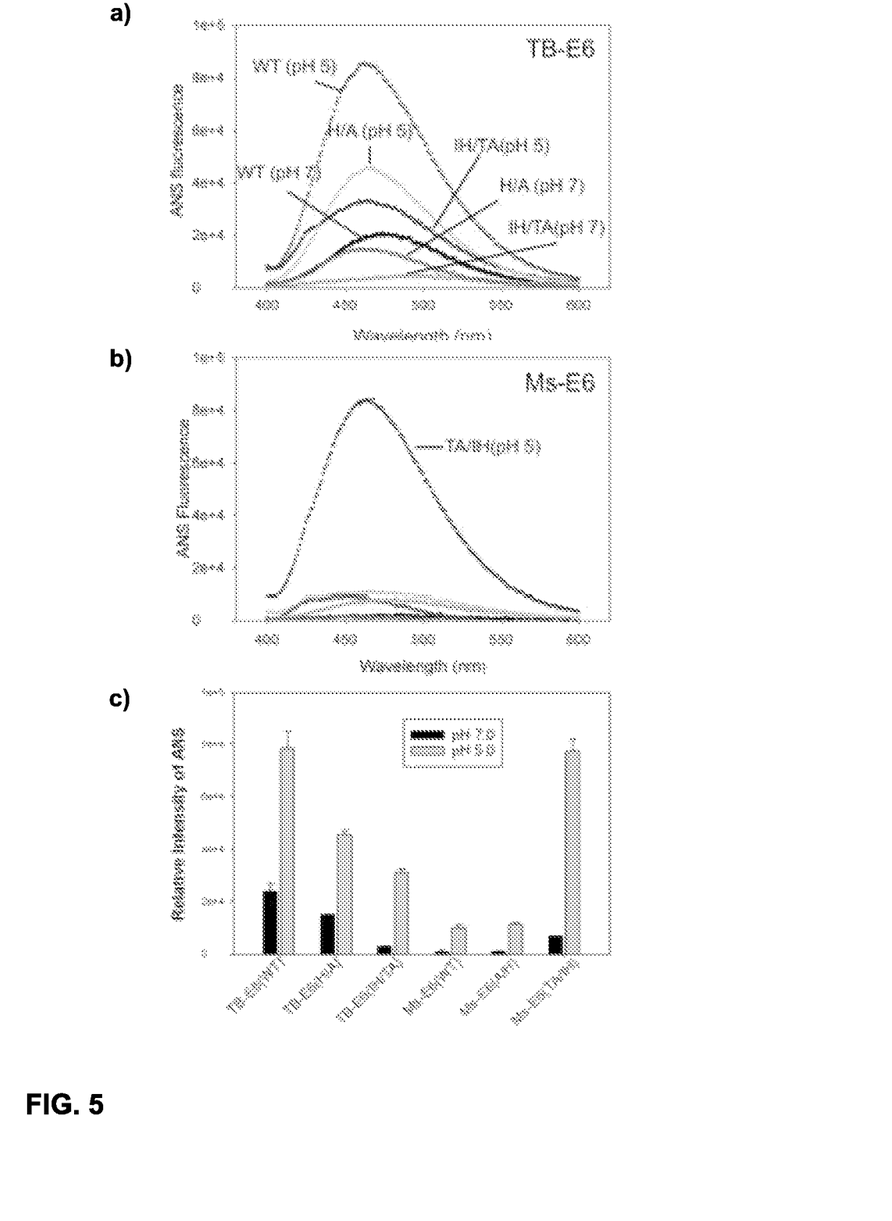
FIG. 5 depicts: a) and b) are graphs of the ANS fluorescence from MtbESAT-6, MsESAT-6 and the indicated mutants at either pH 7 or pH 5 solutions, and c) is a bar graph of ANS-relative intensity at pH 7 or pH 5 from MtbESAT-6, MsESAT-6 and indicated mutants, FIGS. 6a, b, c, and d are graphs of the Trp emission spectra of MtbESAT-6, MsESAT-6 and the indicated mutants at either pH 7 or pH 5 solutions.

The extrinsic fluorescence dye ANS is weakly fluorescent in an aqueous environment but becomes highly fluorescent when it binds to hydrophobic sites of proteins. In our previous report, we successfully used ANS to measure the solvent-exposed hydrophobicity of MtbESAT-6 and MsESAT-6 upon acidification[41,42]. Here, we used ANS to measure the solvent-exposed hydrophobicity of MtbESAT-6, MsESAT-6 and the mutants at either pH 7.0 or 5.0 (FIG. 5). Consistent with previous results, MtbESAT-6(WT) had a significantly increased ANS fluorescence at pH 5, while MsESAT-6(WT) did not. Compared to MtbESAT-6(WT), MtbESAT-6(H/A) and MtbESAT-6(IH/TA) had 40% and 60% reduction in ANS fluorescence at pH 5, respectively. While MsESAT-6(A/H) had a similar ANS fluorescence relative to MsESAT-6(WT), MsESAT-6(TA/IH) exhibited a significantly increased ANS fluorescence to a level that is equivalent to that of MtbESAT-6(WT). The ANS fluorescence result is well correlated to that of ANTS fluorescence dequenching assay.

MsESAT-6(TA/IH) Became Responsive to Acidification, Evidenced by Intrinsic Tryptophan (Trp) Fluorescence.

Figure 6:
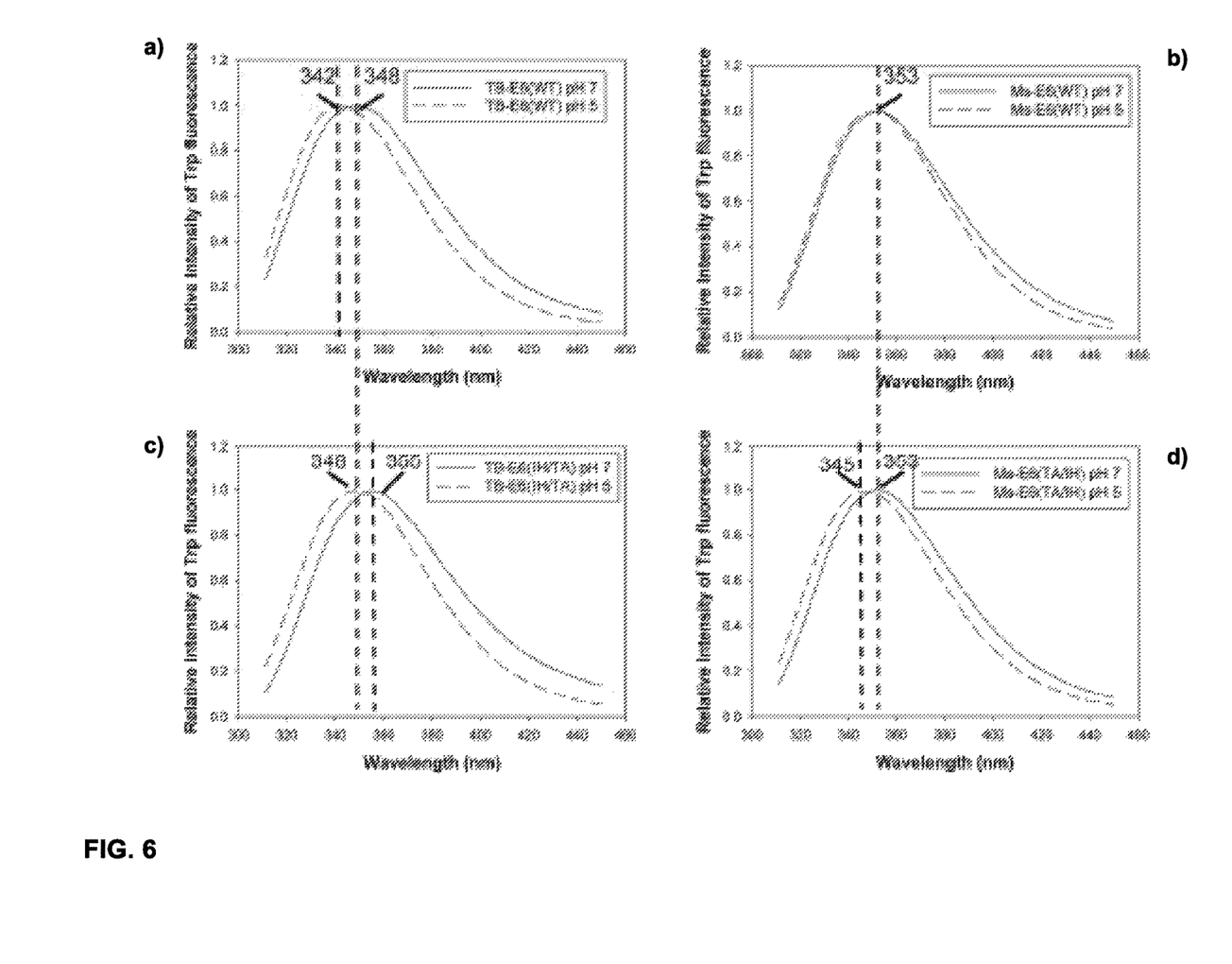

Trp emission spectrum is highly sensitive to solvent polarity. The emission of Trp may be blue-shifted (shorter wavelength) if the residue is buried within a native protein, and its emission may be red-shifted (longer wavelength) when the protein is unfolded. Consistent to our previous studies, MtbESAT-6(WT) had an emission peak at ~348 nm at pH 7, and upon acidification the emission peak was blue-shifted to ~342 nm (FIG. 6a). At pH 7, the emission peak of MsESAT-6(WT) was at ~353 nm, and acidification had little effect on the Trp spectrum (FIG. 6b). As predicted, MsESAT-6(TA/IH) exhibited a blue shift upon acidification (from 353 nm to 345 nm), indicating that this mutant became responsive to pH change (FIG. 6d). Interestingly, we found that at pH 7 the emission peak of MtbESAT-6(IH/TA) was at ~355 nm, while at pH 5 MtbESAT-6(IH/TA) was blue-shifted to ~348 nm, which suggests that MtbESAT-6(IH/TA) had an altered structure than MtbESAT-6(WT) at neutral pH, but it was still able to respond to acidification (FIG. 6c). This result is consistent with the results obtained in the ANTS and ANS experiments. Replacement of TA with IH fully restored MsESAT-6 membrane-interacting activity, but mutating IH to TA only partially reduced the activity of MtbESAT-6, suggesting that additional residue(s) is required.

Mutations at the Residues 17, 38, 67 and 74 Further Reduced the Membrane-Interacting Activity of MtbESAT-6 (IH/TA).

To generate a null-mutant of MtbESAT-6, MtbESAT-6 (IH/TA) was used as the template. Residues A17 to E, K38 to T, N67 to L and R74 to Q, were mutated, one at a time. These residues are located on the central helix-turn-helix motif and have drastically different chemical properties compared to the corresponding residues on MsESAT-6.

Thus, they are more likely to be responsible for the differential membrane-interacting activity between the two proteins shown in FIGS. 3a and 3b.

Compared to MtbESAT-6(IH/TA), all of the mutations further reduced the membrane-interacting activity to various degrees in the ANTS fluorescence dequenching assay (FIG. 7a). Among them, MtbESAT-6(IH/TA-17) had the lowest activity, which is ~20% of MtbESAT-6(IH/TA) and ~12% of MtbESAT-6(WT) by calculation. Consistent results were observed on ANS fluorescence, where mutations at 17, 38, 67 and 74 further reduced the solvent-exposed hydrophobicity, with MtbESAT-6(IH/TA-17) being the lowest (FIG. 7b). Similar to MtbESAT-6(IH/TA), the Trp fluorescence spectrum of MtbESAT-6(IH/TA-17) had a red-shift even at pH 7 (peak emission at ~353 nm), while at pH 5, it underwent a ~10 nm blue-shift with the emission peak at ~342 nm (FIGS. 7c, and 7d). The other three mutants, MtbESAT-6(IH/TA-38), MtbESAT-6(IH/TA-67), and MtbESAT-6(IH/TA-74), had similar spectra relative to MtbESAT-6(IH/TA-17) (data not shown).

MtbESAT-6 and MsESAT-6 share a high sequence homology, but exhibit differential membrane-interacting activities. This observation provides us with an excellent opportunity to identify the key residues essential for membrane interaction. In the present study, by exchanging the different residues between the two ESAT-6 proteins, we found that solely replacing the two residues TA with IH in MsESAT-6 fully restored its membrane-interacting activity, while replacing IH with TA in MtbESAT-6 only partially reduced the activity. Additional mutations at A17, K38, N67 and R74 further reduced the activity, with MtbESAT-6(IH/TA-17) being the lowest.

It was an interesting puzzle that MsESAT-6 is inactive in membrane interaction, but its overall hydrophobicity is equivalent to that of MtbESAT-6. In an earlier pH titration experiment, it was demonstrated that MtbESAT-6 undergoes conformational changes and inserts into the liposomal membranes when pH is dropped below 5. Therefore, it is reasonable to believe that MsESAT-6 lacks the ability to sense the pH change and to make pH-dependent conformational changes.

Histidine has been widely recognized as a pH sensor. The imidazole group of histidine is the only amino acid side chain affected within the physiological pH range. With a pKa at ~6.10, the imidazole group is neutral, apolar and hydrophobic at ~pH 7, but it is protonated and becomes positively charged, polar and hydrophilic at pH 5. Thus, protonation of histidine at low pH usually serves as a trigger for conformational changes. The helical wheel diagram of MtbESAT-6 generated from the solution structure of ESAT-6/CFP-10 heterodimer shows that H26 has intra-molecular interaction with D59 (negatively charged), which is located in the center of Helix 2. It is likely that upon acidification H26 is protonated and becomes positively charged, resulting in attraction between the two residues, which may be the mechanism of initiating conformational changes.

Of note, a single-exchange (A/H) only partly affected the activity, and it required the double-exchange (IH/TA) to fully restore MsESAT-6 activity. In the solution structure of the heterodimer, the hydrophobic I25 has both intra-molecular interaction with L65 on Helix 2 of MtbESAT-6 and inter-molecular interaction with D24 of CFP-10 (FIG. 3b). While the structure for MtbESAT-6 alone in solution is not available, observations (not shown) suggest that MtbESAT-6 forms a homo-complex in solution (probably a dimer). Given that MtbESAT-6 and MtbCFP-10 share 50% homology, it is highly possible that two MtbESAT-6 molecules form an anti-parallel homodimer in a similar manner as the heterodimer. Within the homo-complex, the hydrophobic residues, like I25, should be buried inside the structure and protected away from the solution at neutral pH. Upon acidification, protonation of H26 may trigger a relay of conformational changes that exposes I25 to the solution, which in turn promotes further intra- and inter-molecular conformational changes, as evidenced by the increased hydrophobicity (FIG. 5) and a blue shift of Trp emission spectrum for MsESAT-6(TA/IH) at pH 5 (FIG. 6d).

Figure 7:
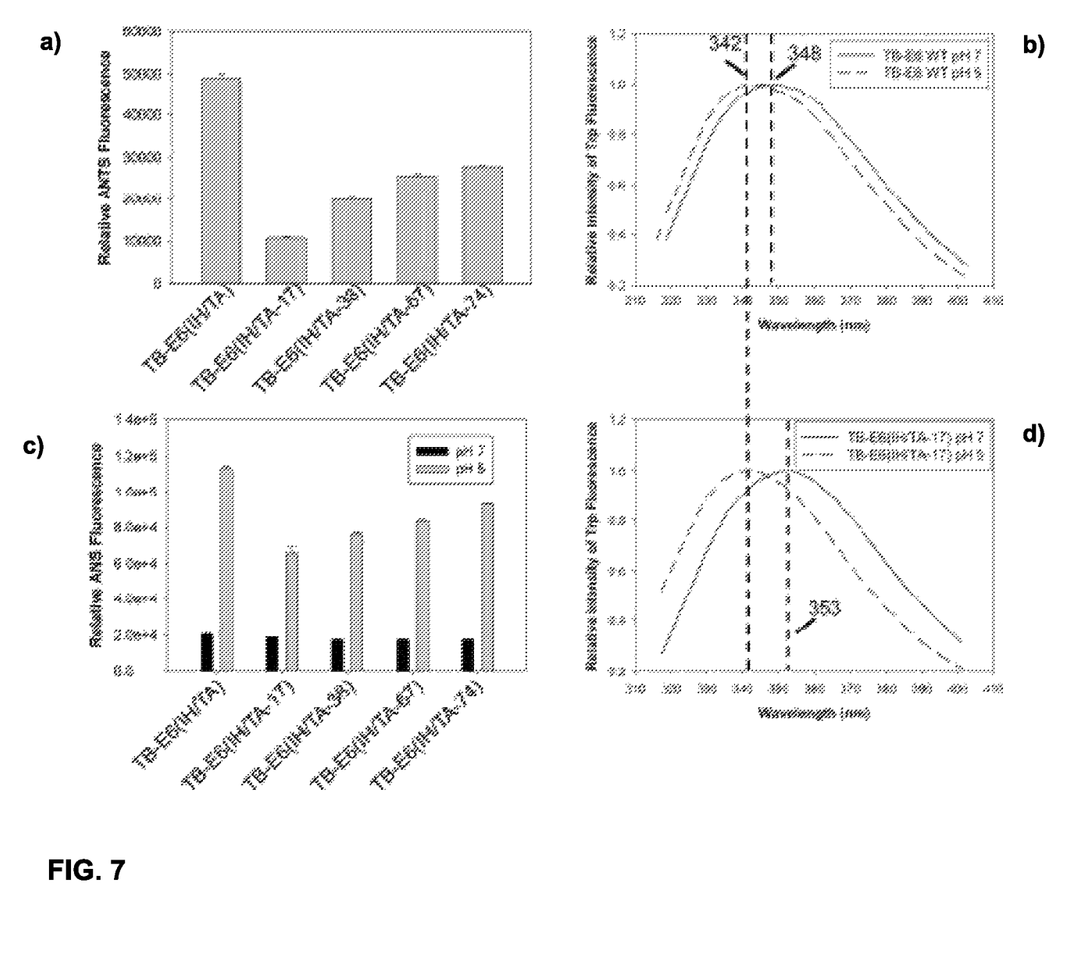

Unlike restoring MsESAT-6 activity, which requires two residues (IH), deletion of MtbESAT-6 activity apparently requires multiple factors (FIG. 7). In fact, this finding is not surprising because as a small-sized protein, the majority of MtbESAT-6 molecule (Helix-turn-Helix motif) is required to insert into the membrane in order to form a membrane-spanning pore. The heterodimer structure (FIG. 3b) and previous helical wheel analysis have shown that A17 and K38 are located on the same interface of Helix 1 with inter-molecular contacts with T35 and E14 of MtbCFP-10, respectively; while N67 and R74 are located on the same surface of Helix 2 without apparent intra- and inter-molecular interaction. Since the structures of MtbESAT-6 homo-complex either at neutral pH (pre-pore) or at acidic pH (pore) are not available, it is not clear how these mutations affect the membrane-interacting activity. Presumably, A17/K38 and N67/R74 are located on the interfaces that are important for intra- and/or inter-molecular interaction, and the mutations at these positions disrupted the interactions. We also noticed that these residues as well as I25-H26 are in close proximity with the hydrophobic residues Leu or Ile, including I18, L28-L29, L65, L69, L72 and I76. These Leu and Ile residues are highly conserved in all of the ESAT-6 orthologs, indicating that they primarily play structural roles. For instance, mutations on L28-L29 resulted in attenuated virulence of M. tuberculosis in mice, which was presumably due to disruption of the MtbESAT-6 structure. Thus, mutations of the residues, such as I25-H26, A17, K38, N67, and R74, are expected to induce significant conformational changes through affecting their adjacent hydrophobic residues (Leu and/or Ile).

Current studies have suggested that the membrane-interacting activity of ESAT-6 proteins is the determining factor for the virulence phenotypes of mycobacteria. Understanding of the underlying mechanism by which MtbESAT-6 contributes to the pathogenesis of M. tuberculosis is of great significance. Here, characterization of the differential membrane-interacting activity between MtbESAT-6 an MsESAT-6 has provided valuable insights into the mechanism of MtbESAT-6 membrane interaction. The identified MtbESAT-6 mutants with attenuated or deleted membrane-interacting activity will lead to development of novel therapeutics or vaccines against TB.

Example 3: Vaccine and Other Pharmaceutical Compositions and Administration

The present invention includes methods for preventing or ameliorating mycobacterial infections. As such, the invention contemplates vaccines for use in both active and passive immunization embodiments. Immunogenic compositions, proposed to be suitable for use as a vaccine, may be prepared from immunogenic ESAT-6 polypeptide(s).

In certain aspects the ESAT-6 protein is mutated at one or more residues. In certain aspects the mutate ESAT-6 protein is less virulent or cytotoxic. An ESAT-6 composition can comprise one or more adjuvants. In certain aspects the ESAT-6 protein comprises 1, 2, or 3 amino acid substitutions. In certain aspects, the substitutions are at amino acids corresponding to positions 5, 25, and/or 26 of SEQ ID NO:1. In certain aspects, the ESAT-6 protein contains an amino acid substitution at residue 5 (Q5) of SEQ ID NO:1. In a further aspect a mutant ESAT-6 protein comprises a lysine (Q5K) or arginine (Q5R) substitution corresponding to Q5 of SEQ ID NO:1. In certain aspects a mutant ESAT-6 protein comprises a threonine (I25T) substitution corresponding to I25 of SEQ ID NO: 1. In certain aspects a mutant ESAT-6 protein comprises an alanine (H26A) substitution corresponding to H26 of SEQ ID NO: 1. In certain aspects the ESAT-6 protein has an amino acid substitution at position 5; position 25; position 26; positions 5 and 25; positions 5 and 26; position 25 and 26; or positions 5, 25, and 26. In certain aspects the amino acid substitution is selected form the remaining 19 naturally occurring amino acids. In a further aspect the substitution is a conservative or non-conservative substitution. In still a further aspect, the substitution is a Q5K, Q5R, I25T, H26A substitution of a combination thereof.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredients required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064.

Carriers—

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

Adjuvants—

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against a variant ESAT-6 polypeptide or any other bacterial protein or combination contemplated herein. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles [e.g., mannide mono-oleate (Aracel A)]; or emulsion with a 20% solution of a perfluorocarbon (Fluosol-DA®) used as a block substitute may also be employed to produce an adjuvant effect.

Examples of and often used adjuvants include complete Freund's adjuvant (a non-specific stimulator of the immune response containing killed *Mycobacterium tuberculosis*), incomplete Freund's adjuvants, and aluminum hydroxide.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m2) (Johnson/Mead, NJ) and cytokines such as γ-interferon, IL-2, or IL-12 or genes encoding proteins involved in immune helper functions, such as B-7.

Compositions of the present disclosure include immunogenic compositions wherein the antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in subjects (humans, other mammals etc.).

Based on the aforementioned examples, in another aspect of the disclosure, additional therapeutics or vaccines which include all possible mutations (the 19 amino acids other than glutamine) at the residue Glutamine 5 (Q5) of ESAT-6 are contemplated to be within the scope of this disclosure.

In yet another aspect of the disclosure, all possible mutations (the 19 amino acids other than Leucine and the 19 amino acids other than Histidine) at the residues I25H26 of ESAT-6 are contemplated to be within the scope of this disclosure.

Furthermore, DNA vaccines carrying the ESAT-6 gene with the DNA sequence modifications to encode the various amino acid mutations noted herein are contemplated to be within the scope of this disclosure.

While traditional methods for vaccine development have focused on using BCG, any vector carrying the ESAT-6 gene with the mutations specified above, may be used to generate the compositions described herein.

As described herein, the methods and compositions disclosed herein can be used as to prevent and treat both latent and active tuberculosis.

Furthermore, while the present disclosure teaches compositions and related methods for TB vaccination in humans, the scope of the disclosure encompasses other organisms, including animals such as a wide variety of commercially important mammals (e.g. veterinary treatment and prevention of TB in cattle, horses etc.).

Also, the present disclosure teaches methods for diagnosing TB exposure in organisms, such as humans.

In light of the principles and example embodiments described and illustrated herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise.

Similarly, although example processes have been described with regard to particular operations performed in a particular sequence, numerous modifications could be applied to those processes to derive numerous alternative embodiments of the present invention. For example, alternative embodiments may include processes that use fewer than all of the disclosed operations, processes that use additional operations, and processes in which the individual operations disclosed herein are combined, subdivided, rearranged, or otherwise altered.

This disclosure may include descriptions of various benefits and advantages that may be provided by various embodiments. One, some, all, or different benefits or advantages may be provided by different embodiments. In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A *Mycobacterium tuberculosis* variants with mutations in the 6-kDal early secreted antigenic target (ESAT-6) protein, wherein the *M. tuberculosis* exhibits attenuated virulence in a mammal when compared to the *M. tuberculosis* with wild type ESAT-6, wherein the ESAT-6 protein variant comprises a glutamine to lysine or arginine substitution at the amino acid position corresponding to position 5 (Q5K) or (Q5R) of SEQ 1D NO: 1.

2. The *M. tuberculosis* of claim 1, wherein the *M. tuberculosis* is capable of protecting the mammal from challenge by a virulent *M. tuberculosis*.

3. The *M. tuberculosis* of claim 1, wherein the ESAT-6 protein variant further comprises 1 or 2 amino acid substitution at an amino acid position selected from amino acid 25 or 26 of SEQ 1D NO: 1.

4. The *M. tuberculosis* of claim 1, wherein the ESAT-6 protein variant further comprises an isoleucine to threonine substitution at the amino acid corresponding to position 25 (I25T) of SEQ 1D NO: 1.

5. The *M. tuberculosis* of claim 1, wherein the ESAT-6 protein variant further comprises a histidine to alanine substitution at the amino acid corresponding to position 26 (H26A) of SEQ 1D NO: 1.

6. The *M. tuberculosis* of claim 1, wherein the ESAT-6 protein variant further comprises a alanine to glutamic acid substitution at the amino acid corresponding to position 17 (A17E) of SEQ 1D NO: 1.

7. The *M. tuberculosis* of claim 1, wherein the ESAT-6 protein variant further comprises a lysine to threonine substitution at the amino acid corresponding to position 38 (K38T) of SEQ 1D NO: 1.

8. The *M. tuberculosis* of claim 1, wherein the ESAT-6 protein variant further comprises an asparagine to leucine substitution at the amino acid corresponding to position 67 (N67L) of SEQ 1D NO: 1.

9. The *M. tuberculosis* of claim 1, wherein the ESAT-6 protein variant further comprises an arginine to glutamine substitution at the amino acid corresponding to position 74 (R74Q) of SEQ 1D NO: 1.

10. A *mycobacterium* in the *Mycobacterium tuberculosis* complex, genetically engineered to express ESAT-6 protein comprising glutamine to lysine or arginine substitution at an amino acid position corresponding to position 5, (Q5K) or (Q5R) of SEQ 1D NO: 1.

11. A *mycobacterium* ESAT-6 protein comprising glutamine to lysine or arginine substitution at an amino acid position corresponding to position 5 (Q5K) or (Q5R) of SEQ 1D NO: 1.

12. A The *mycobacterium* ESAT-6 protein of claim 11, further comprising an isoleucine to threonine substitution at the amino acid position corresponding to position 25 (I25T) of SEQ 1D NO: 1.

13. The *mycobacterium* ESAT-6 protein of claim 11, further comprising a histidine to alanine substitution at the amino acid corresponding to position 26 (H26A) of SEQ 1D NO: 1.

14. A tuberculosis vaccine comprising the *M. tuberculosis* of claim 1 in a pharmaceutically acceptable excipient.

15. A tuberculosis vaccine comprising the *mycobacterium* of claim 10 in a pharmaceutically acceptable excipient.

16. A tuberculosis vaccine comprising the *mycobacterium* ESAT-6 protein of claim 11 in a pharmaceutically acceptable excipient.

* * * * *

SEQUENCE LISTING

```
<160> NUMBER OF SEQ ID NOS: 1

<210> SEQ ID NO 1
<211> LENGTH: 95
<212> TYPE: PRT
<213> ORGANISM: Mycobacterium tuberculosis
```

```
<400> SEQUENCE: 1

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Ile Asp Glu Gly
                20                  25                  30

Lys Gln Ser Leu Thr Lys Leu Ala Ala Trp Gly Gly Ser Gly Ser
            35                  40                  45

Glu Ala Tyr Gln Gly Val Gln Gln Lys Trp Asp Ala Thr Ala Thr Glu
        50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95
```